(12) United States Patent
Sorensen

(10) Patent No.: US 8,512,370 B2
(45) Date of Patent: Aug. 20, 2013

(54) PILLOW WITH PLURALITY OF BALLS FOR RELIEVING SINUS AND CONGESTION

(76) Inventor: Susan M. Sorensen, Burbank, CA (US)

( * ) Notice: Subject to any disclaimer, the term of this patent is extended or adjusted under 35 U.S.C. 154(b) by 240 days.

(21) Appl. No.: 13/006,372

(22) Filed: Jan. 13, 2011

(65) Prior Publication Data

US 2012/0053618 A1 Mar. 1, 2012

Related U.S. Application Data

(60) Provisional application No. 61/378,632, filed on Aug. 31, 2010.

(51) Int. Cl.
*A61B 17/00* (2006.01)

(52) U.S. Cl.
USPC ............. 606/204; 607/109; 601/39; 601/115; 601/131; 606/201; 606/204.15

(58) Field of Classification Search
USPC ........ 606/201–204, 24.15; 607/96, 108–111; 601/39, 115, 131
See application file for complete search history.

(56) References Cited

U.S. PATENT DOCUMENTS

| 5,344,437 | A | * | 9/1994 | Pistay | 607/109 |
| 5,628,772 | A | * | 5/1997 | Russell | 607/109 |
| 6,007,501 | A | * | 12/1999 | Cabados et al. | 601/15 |
| 2006/0036305 | A1 | * | 2/2006 | Koby et al. | 607/109 |

* cited by examiner

*Primary Examiner* — Gary Jackson
*Assistant Examiner* — Sidharth Kapoor

(57) ABSTRACT

The present invention provides a head-rest pillow that aids the user in sleeping by relieving their sinus congestion discomfort and snoring that may be associated with such congestion. The pillow comprises a core layer that has plurality of firm balls sewn in it forming compartmentalized section. The core layer is covered with a batting layer that is sewn all around the core layer for purposes of cushioning and providing comfort to the user. This combination of core and batting layer and inserted in a hollow pillow case that covers the core and batting layer, providing a head-rest pillow for a user to use.

9 Claims, 2 Drawing Sheets

PILLOW WITH PLURALITY OF BALLS FOR RELIEVING SINUS AND CONGESTION

CROSS-REFERENCE TO RELATED APPLICATIONS

Provisional Application for Open Airways Acupressure Sinus Pillow Application No. 61/378,632 filed on Aug. 31, 2010 by Susan Michelle Sorensen

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISC APPENDIX

Not applicable.

BACKGROUND OF THE INVENTION

In the search for a safe, simple, non-medical, but effective aide that relieves or reduces nighttime sinus congestion and thereby helps to reduce snoring that may be associated with such sinus congestion.

Many products approach the problem with chemicals—nasal sprays, sinus pills, etc. Other products try to mechanically open the nasal passages (adhesive strips on the outside of nasal septum, clips that push outward from inside nasal passages). Still other products work on positioning the head; that is, designing pillows or other apparatus that that force one's head into the optimal position for nighttime breathing.

Many products have tried to relieve the nighttime breathing issue. This product's intent is to provide relief and "open airways" using a non-medical, non-chemical remedy involving simple pressure to sinus "pressure points" on the head.

BRIEF SUMMARY OF THE INVENTION

The Open Airways® Acupressure Sinus Pillow is designed to provide a non-medical, safe and uncomplicated alternative to other products for relieving nighttime sinus congestion discomfort and the snoring that may be associated with such congestion. The Open Airways® Acupressure Sinus Pillow uses simple pressure to the head, on numerous sinus "pressure points." Pressure is applied by the firm balls constructed into the pillow simply by resting one's head on the pillow.

BRIEF DESCRIPTION OF THE VIEW OF DRAWINGS

Figure 1:
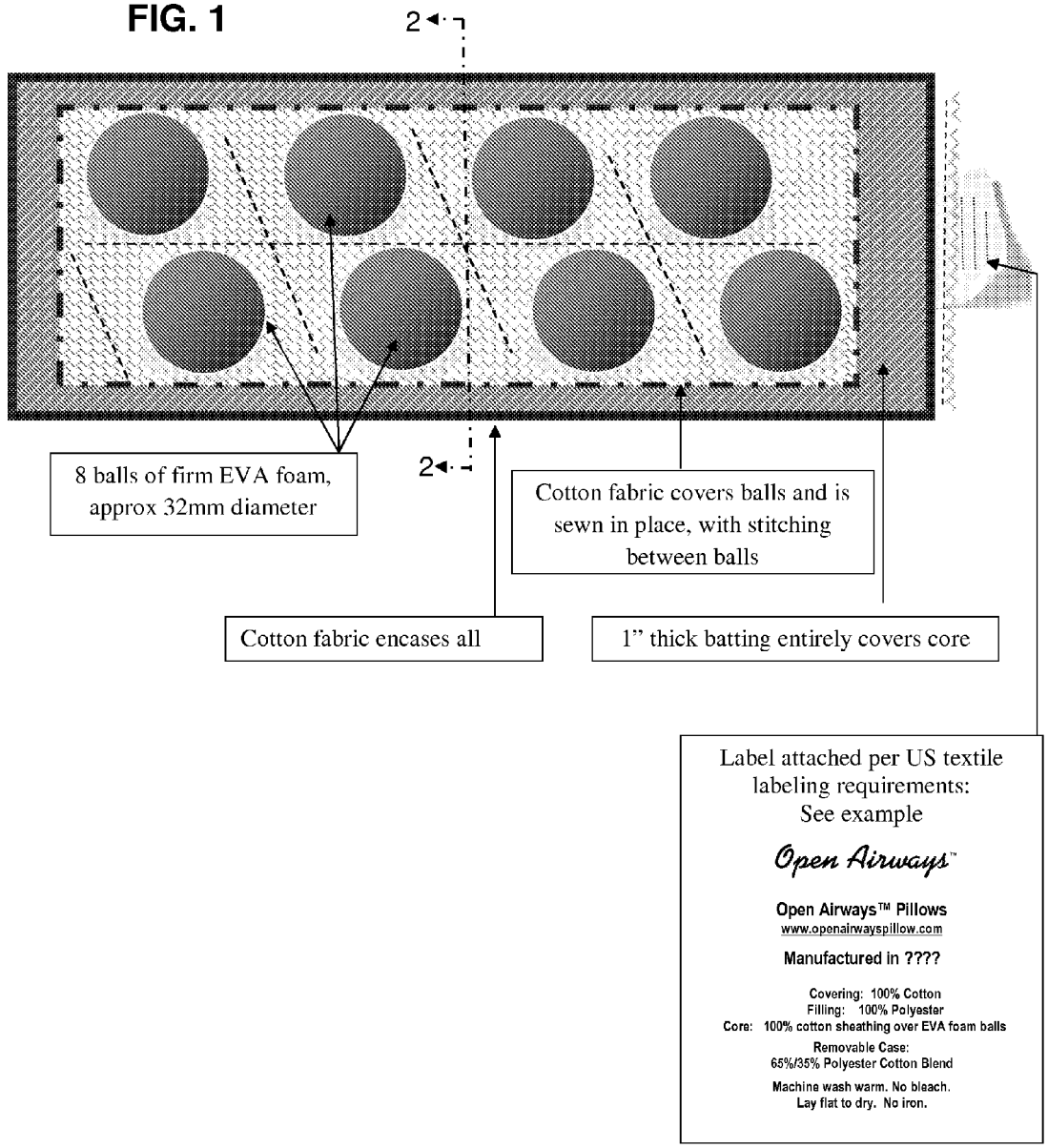

In FIG. 1, you see the general framework of the Open Airways® Acupressure Sinus Pillow. It consists of the firm rubber balls, spaced evenly in two rows, covered by a polyfill batting and sewn into place to prevent the balls from moving within the pillow. This becomes the core of the pillow. More pillow batting or filling is placed around the pillow core, and then a pillow cover is sewn over all. The product also comes with a removable, washable pillowcase.

Figure 2:
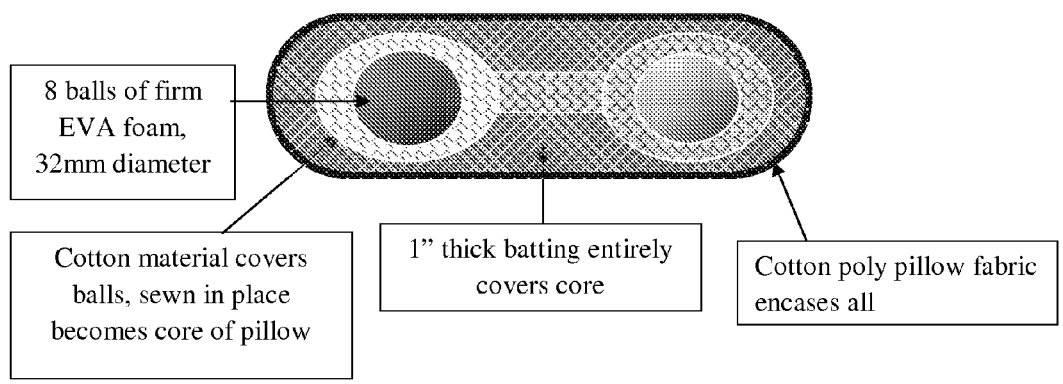

In FIG. 2, you see a cross section of the pillow. In the center, is the ball—showing the top row—the second row as shown somewhat in shadow. There is a layer of material completely surrounding the balls with stitching between the balls to hold them in place. Another layer of batting covers the core and a final layer of fabric encloses the entire pillow.

DETAILED DESCRIPTION OF THE INVENTION

The Open Airways® Acupressure Sinus Pillow is made starting with the nine firm rubber balls 32 mm in diameter. Then ½" thick poly fiberfill batting is placed entirely around the balls and sewn into place as indicated in FIG. 1. An additional one inch of poly fiberfill batting is placed entirely around the ball core, and tacked or glued into place. Cotton-poly blend fabric is then sewn around the entire pillow creating a completely enclosed pillow of about 12 inches in length, 4.5 inches across and about 2.5 inches in depth. The user is also supplied with a washable cotton or cotton-poly blend pillow case, which covers the entire pillow and may be easily removed for washing.

Whereas the Open Airways® Acupressure Sinus Pillow has been described herein with respect to particular specifications, it should be understood that various changes and modifications may be suggested and this patent is intended to encompass such changes and modifications as fall within the scope of this or any appended claims.

The pillow is used as follows. User places the Open Airways® Acupressure Sinus Pillow on top of their regular pillow. If lying on their side, they position the pillow above their earlobe. If lying on their back, they position the pillow above their neckline. The pressure is applied simply by resting one's head on the firm balls constructed into the pillow. Users may adjust or re-position as needed to improve the pillow's effect through greater or more numerous balls coming into contact with sinus pressure points found all along the hairline and skull. Airways usually open within minutes of pressure being applied from the pillow. For best results users are to make sure one or more balls in pillow press firmly against head.

During night the pillow may slip. Users should simply reposition the Open Airways® Acupressure Sinus Pillow anytime they need opening of their sinus airways or when they are informed (by their spouse, neighbors or whomever) that they are snoring.

The invention claimed is:

1. A head-rest pillow for relieving nighttime sinus congestion discomfort and snoring comprising:
   a core that forms a first layer of the pillow;
      wherein the core has a top layer, a bottom layer, and a plurality of firm balls that are entirely sewn between the top and the bottom layer such that they are compartmentalized into sections;
   a batting layer that forms a second layer that overlays the top layer and the bottom layer of the core and is sewn on the top layer and the bottom layer of the core for purposes of cushioning and comfort; and
   a hollow pillow case having a longitudinal slit running across length of the pillow case that allows placement of the core and the batting layer therein.

2. The head-rest pillow of claim 1, wherein the plurality of firm balls sewn between the top and the bottom layer of the core are spaced evenly in two rows.

3. The head-rest pillow of claim 2, wherein each row consists of at least four firm balls.

4. The head-rest pillow of claim 1, wherein each of the plurality of firm balls are about 32 millimeters in diameter.

5. The head-rest pillow of claim 1, wherein the batting layer comprises of polyol fiberfill material which is at least half inch thick.

6. The head-rest pillow of claim 1, wherein the pillow will have dimensions of at least 12 inches in length, 4.5 inches in width, and 2.5 inches in thickness.

7. The head-rest pillow of claim 1, wherein the plurality of firm balls are made of rubber.

8. The head-rest pillow of claim 1, wherein the plurality of firm balls sewn in compartmentalized sections of the core result in little or no movement of the balls.

9. A method for using a head-rest pillow that relieves nighttime sinus congestion discomfort and snoring comprising:
- placing a pillow on a bed;
- placing the head-rest pillow as described in claim 1 on top of the pillow;
- adjusting the head-rest pillow to be placed above a user's neckline and above the user's earlobe for purposes of allowing appropriate distribution of pressure applied by the firm balls.

\* \* \* \* \*